(12) United States Patent
Manku et al.

(10) Patent No.: US 8,936,803 B2
(45) Date of Patent: Jan. 20, 2015

(54) PHARMACEUTICAL COMPOSITIONS COMPRISING DGLA AND/OR 15-HETRE AND METHODS OF USE THEREOF

(71) Applicant: Dignity Sciences Limited, Dublin (IE)

(72) Inventors: Mehar Manku, Birmingham (GB); John Climax, Dublin (IE); David Coughlan, Dublin (IE)

(73) Assignee: Dignity Sciences Limited, Dublin (IE)

( * ) Notice: Subject to any disclaimer, the term of this patent is extended or adjusted under 35 U.S.C. 154(b) by 8 days.

(21) Appl. No.: 13/655,892

(22) Filed: Oct. 19, 2012

(65) Prior Publication Data

US 2013/0101533 A1 Apr. 25, 2013

Related U.S. Application Data

(63) Continuation of application No. 61/549,022, filed on Oct. 19, 2011.

(51) Int. Cl.
| | | |
|---|---|---|
| *A01N 25/26* | (2006.01) | |
| *A61K 31/202* | (2006.01) | |
| *A61K 9/00* | (2006.01) | |
| *A61K 47/10* | (2006.01) | |
| *A61K 8/36* | (2006.01) | |
| *A61Q 17/04* | (2006.01) | |

(52) U.S. Cl.
CPC ............. *A61K 31/202* (2013.01); *A61K 9/0014* (2013.01); *A61K 47/10* (2013.01); *A61K 8/361* (2013.01); *A61Q 17/04* (2013.01)
USPC .......................................................... 424/420

(58) Field of Classification Search
None
See application file for complete search history.

(56) References Cited

U.S. PATENT DOCUMENTS

2003/0194446 A1* 10/2003 Akes et al. ..................... 424/642

FOREIGN PATENT DOCUMENTS

WO WO 2010125340 A1 * 11/2010 ........... A61K 31/202

OTHER PUBLICATIONS

Erythema, Retrieved online [Feb. 11, 2014], Retrieved from URL:<http://umm.edu/health/medical/altmed/condition/erythema>.*

* cited by examiner

*Primary Examiner* — Lezah Roberts
*Assistant Examiner* — Nannette Holloman
(74) *Attorney, Agent, or Firm* — Perkins Coie LLP

(57) ABSTRACT

The present disclosure provides compositions comprising fatty acids, or derivatives thereof (e.g., C1-C4 esters) including, for example, DGLA, and/or 15-HETrE, used singly or in combination for the prevention and/or treatment of effects associated with UV radiation such as erythema.

10 Claims, 12 Drawing Sheets

PHARMACEUTICAL COMPOSITIONS COMPRISING DGLA AND/OR 15-HETRE AND METHODS OF USE THEREOF

PRIORITY CLAIM

This application claims priority to, and the benefit of, U.S. Application No. 61/549,022, filed Oct. 19, 2011, the entirety of which is incorporated herein by reference.

FIELD

The disclosure generally relates to compositions comprising fatty acids including, for example, DGLA, 15-OHEPA, and/or 15-HETrE and their use for preventing and/or treating the effects associated with UV radiation such as erythema.

BACKGROUND

Ultraviolet (UV) radiation is the most prominent and ubiquitous carcinogen in our environment and the skin is its major target. Epidemiological, clinical and biological studies have implicated repeated exposures of human skin to solar UV radiation as a cause of both melanoma and non-melanoma skin cancers. UV radiation also induces inflammatory responses including erythema, edema, dermal infiltration of leukocytes and production of cytokines and growth factors. Further, there is mounting evidence that such inflammation plays a pivotal role in tumor initiation and promotion. Accordingly, there exists a need in the art for methods for protecting the skin against UV-induced damage and its effects.

SUMMARY

The present disclosure provides compositions comprising fatty acids agents including, for example, DGLA, 15-OHEPA, and/or 15-HETrE, used singly or in combination, for the prevention and/or treatment of effects associated with UV radiation such as erythema. Optionally, such compositions may further comprise one or more sunscreen active agents.

The present disclosure provides compositions, for preventing or reducing the occurrence of erythema, that comprise a therapeutically effective amount of DGLA and/or 15-HETrE.

In some embodiments, the composition comprises about 0.1 wt. % DGLA to about 20 wt. % DGLA.

In some embodiments, the composition comprises about 10 wt. % DGLA, about 1.0 wt. % DGLA, or about 0.1 wt. % DGLA.

In some embodiments, the composition comprises about 0.01 wt. % to about 50 wt. % 15-HETrE.

In some embodiments, the composition comprises about 10 wt. % 15-HETrE, about 1.0 wt. % 15-HETrE, about 0.1 wt. % 15-HETrE, or about 0.01 wt. % 15-HETrE.

In some embodiments, the composition comprise about 0.1 wt. % DGLA to about 20 wt. % DGLA and about 0.01 wt. % to about 50 wt. % 15-HETrE.

The present disclosure also provides a photoprotective composition, for preventing or reducing the occurrence of erythema, that comprises i.) a therapeutically effective amount of DGLA and/or 15-HETrE; and ii.) a sunscreen active agent.

In some embodiments, the composition comprises about 0.1 wt. % DGLA to about 20 wt. % DGLA.

In some embodiments, the composition comprises about 10 wt. % DGLA, about 1.0 wt. % DGLA, or about 0.1 wt. % DGLA.

In some embodiments, the composition comprises about 0.1 wt. % to about 50 wt. % 15-HETrE.

In some embodiments, the composition comprises about 10 wt. % 15-HETrE, about 1.0 wt. % 15-HETrE, about 0.1 wt. % 15-HETrE, or about 0.01 wt. % 15-HETrE.

In some embodiments, the composition comprise about 0.1 wt. % DGLA to about 20 wt. % DGLA and about 0.01 wt. % to about 50 wt. % 15-HETrE.

In some embodiments, the sunscreen active agent is a UV blocker, UV absorber, or UV scattering agent.

In some embodiments, the UV blocker is a UVA, UVB, or a UVA/UVB blocker.

In some embodiments, the UV blocker is selected from the group consisting of: para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetra methylbutyl phenol, and bis-ethylhexyloxyphenol methoxyphenyltriazine, 4-methylbenzylidenecamphor, and isopentyl 4-methoxycinnamate.

In some embodiments, the composition further comprises a waterproofing polymer.

The present disclosure also provides methods for preventing or reducing the occurrence of erythema on at least one area of the skin of a subject, comprising: topically applying a therapeutically effective amount of a composition comprising DGLA or 15-HETrE to the at least one area of skin of the subject.

In some embodiments, the composition comprises about 1.0 wt. % DGLA to about 20 wt. % DGLA.

In some embodiments, the composition comprises about 10 wt. % DGLA, about 1.0 wt. % DGLA, or about 0.1 wt. % DGLA.

In some embodiments, the composition comprises about 0.1 wt. % to about 50 wt % 15-HETrE.

In some embodiments, the composition comprises about 10 wt. % 15-HETrE, about 1.0 wt. % 15-HETrE, about 0.1 wt. % 15-HETrE, or about 0.01 wt. % 15-HETrE.

In some embodiments, the erythema is caused by exposure to UV radiation.

In some embodiments, the compositions is topically applied to at least one area of the skin prior to exposure of the subject to UV radiation.

In some embodiments, the composition is applied the skin on a face, arms, torso, or legs.

In some embodiments, the composition further comprises a sunscreen active agent.

In some embodiments, the sunscreen active agent is a UV blocker, UV absorber, or UV scattering agent.

The present disclosure also provides methods for preventing or reducing sun-induced damage of the skin of a subject, comprising: topically applying the composition comprising DGLA or 15-HETrE to the at least one area of skin of the subject.

In some embodiments, the composition comprises about 1.0 wt. % DGLA to about 20 wt. % DGLA.

In some embodiments, the composition comprises about 10 wt. % DGLA, about 1.0 wt. % DGLA, or about 0.1 wt. % DGLA.

In some embodiments, the composition comprises about 0.1 wt. % to about 50 wt. % 15-HETrE.

In some embodiments, the composition comprises about 10 wt. % 15-HETrE, about 1.0 wt. % 15-HETrE, about 0.1 wt. % 15-HETrE, or about 0.01 wt. % 15-HETrE.

In some embodiments, the compositions is topically applied to at least one area of the skin prior to exposure of the subject to sun light.

In some embodiments, the composition is applied the skin on a face, arms, torso, or legs.

In some embodiments, the composition further comprises a sunscreen active agent.

In some embodiments, the sunscreen active agent is a UV blocker, UV absorber, or UV scattering agent.

In some embodiments, the sun-induced damage is photoaging of the skin.

The present disclosure also provides methods for increasing the Sun Protection Factor (SPF) of a sunscreen, comprising: adding a composition comprising DGLA and/or 15-HETrE to the sunscreen.

In some embodiments, the composition comprises about 1.0 wt. % DGLA to about 20 wt. % DGLA.

In some embodiments, the composition comprises about 10 wt. % DGLA, about 1.0 wt. % DGLA, or about 0.1 wt. % DGLA.

In some embodiments, the composition comprises about 0.1 wt. % to about 50 wt. % 15-HETrE.

In some embodiments, the composition comprises about 10 wt. % 15-HETrE, about 1.0 wt. % 15-HETrE, about 0.1 wt. % 15-HETrE, or about 0.01 wt. % 15-HETrE.

In some embodiments, the SPF of the sunscreen is increased to about 10, about 15, about 20, about 25, about 30, about 35, about 40, about 45, about 50, about 55, about 60, about 65, about 70, or about 75.

The present disclosure also provides methods for preventing or reducing the deleterious effects of UV radiation that contacts a surface, comprising: applying to the surface a composition comprising DGLA and/or 15-HETrE.

In some embodiments, the surface is skin.

These and other embodiments of the invention are described in further detail below.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 1:
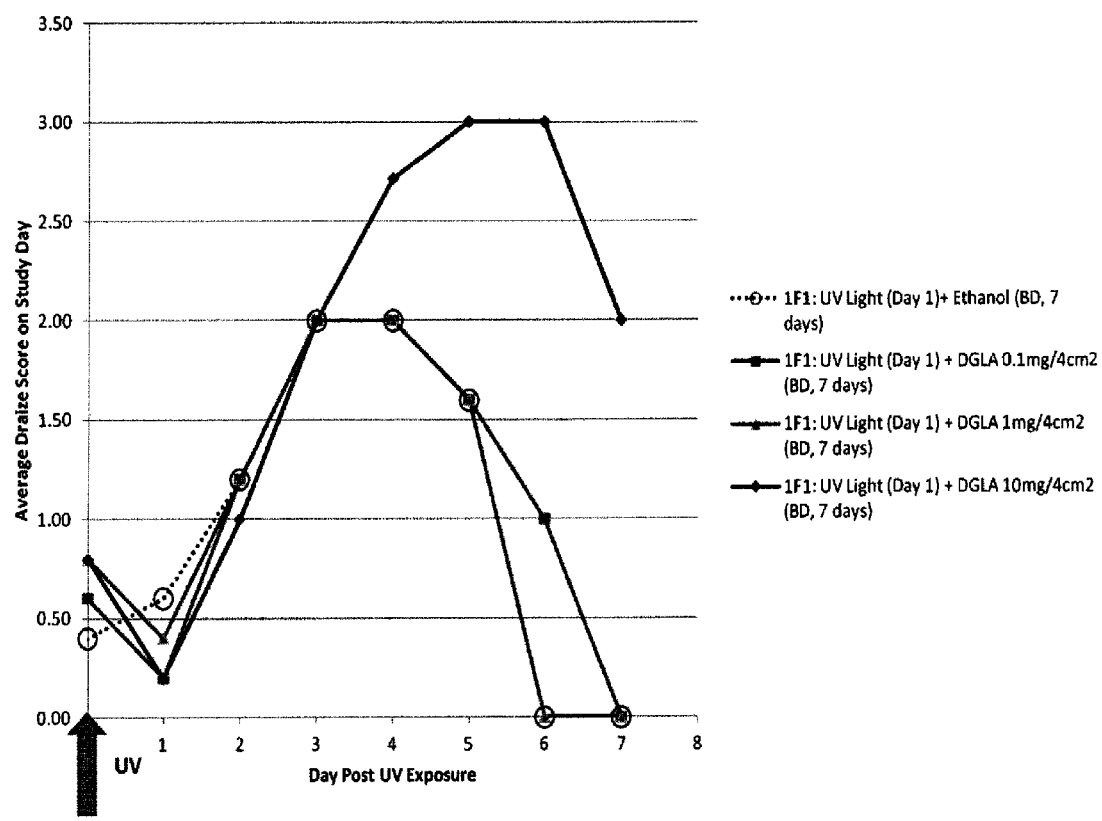
FIG. 1 shows a graphical representation of the average daily Draize score for selected areas of the skin of miniature swine #1 exposed to UV and then topically administered a composition comprising ethanol (vehicle), 1 mg/mL DGLA, 10 mg/mL DGLA, or 100 mg/mL DGLA twice daily for each of seven days.

The present disclosure provides compositions (e.g., pharmaceutical compositions) and formulations that comprise fatty acid agents including, for example, DGLA, 15-OHEPA and/or 15-HETrE. Such agents have been unexpectedly found to prevent and/or treat the effects associated with exposure to ultra-violet (UV) radiation including, for example, erythema.

The present disclosure provides compositions comprising fatty acids including, for example, DGLA, 15-OHEPA and/or 15-HETrE in free acid or derivative form, used singly or in combination with a sunscreen active agent including, for example, a UV blocker (e.g., a UVA, a UVB, or a UVA/UVB blocker), UV absorber, or UV scattering agent. In some embodiments, the composition comprises about 0.1 wt. % DGLA to about 20 wt. % DGLA (e.g., about 10 wt. % DGLA, about 1.0 wt. % DGLA, or about 0.1 wt. % DGLA) or a derivative thereof. In some embodiments, the composition comprises about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE) or a derivative thereof. In some embodiments, the composition comprise about 0.1 wt. % DGLA to about 20 wt. % DGLA (e.g., about 10 wt. % DGLA, about 1.0 wt. % DGLA, or about 0.1 wt. % DGLA) or a derivative thereof and about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE) or a derivative thereof.

UV blockers contemplated for use in the present disclosure may include, but are not limited to, para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetra methylbutyl phenol, and bis-ethylhexyloxyphenol methoxyphenyltriazine, 4-methylbenzylidenecamphor, and isopentyl 4-methoxycinnamate.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Dihomo-gamma-linolenic acid, also known as cis-8,11,14-eicosatrienoic acid or C 20:3ω6 ("DGLA"), is the elongation product of gamma-linolenic acid, also referred to as gamoleic acid or C 18:3ω6 ("GLA"). GLA is a component of natural oils from a variety of plants such as Echium, blackcurrant, borage, evening primrose, hackelia, trichodesma, and buglossoides, to name a few. As used herein, the term "DGLA" refers to DGLA free acid (e.g., cis-8,11,14-eicosatrienoic acid) and/or a pharmaceutically acceptable ester, derivative, conjugate or salt thereof, or mixtures of any of the foregoing. In some embodiments, DGLA is in the form of a $C_{1-4}$ alkyl ester such as methyl ester or ethyl ester form.

15-Hydroxy-eicosa-5,8,11,13,17-pentaenoic acid ("15-OHEPA") is a derivative of EPA. As used herein, the term "15-OHEPA" refers to 15-OHEPA in its free acid form (e.g., 15-hydroxy-eicosa-5,8,11,13,17-pentaenoic acid) and/or a pharmaceutically acceptable ester, derivative, conjugate or salt thereof, or mixtures of any of the foregoing. In some embodiments, the 15-OHEPA is in the form of a $C_{1-4}$ alkyl ester such as methyl ester or ethyl ester form.

15-Hydroxy-eicosa-8(Z),11(Z),13(E)-trienoic acid ("15-HETrE") is a derivative of DGLA. As used herein, the term "15-HETrE" refers to 15-HETrE in its free acid form (e.g., 15-hydroxy-eicosa-8(Z),11(Z),13(E)-trienoic acid) and/or a pharmaceutically acceptable ester, derivative, conjugate or salt thereof; or mixtures of any of the foregoing.

As used herein, the terms "DGLA derivative" and "derivative of DGLA" refer to compounds formed from the chemical conversion of DGLA including, without limitation, 15-HETrE, and esters, derivatives, conjugates or salts thereof; or mixtures of any of the foregoing. One of skill in the art will readily recognize from the chemical structure and other properties whether a given compound is a DGLA derivative.

In one embodiment, DGLA, 15-OHEPA, and/or 15-HETrE is deodorized prior to use in a method or composition as disclosed herein. In one embodiment, crude DGLA, 15-OHEPA, and/or 15-HETrE is mixed with silica and charcoal. In one embodiment, the silica and charcoal are in a ratio of about 1:1 to about 50:1, for example about 1:1, about 2:1, about 3:1, about 4:1, about 5:1, about 6:1, about 7:1, about 8:1, about 9:1, about 10:1, about 12:1, about 14:1, about 15:1, about 16:1, about 18:1, about 20:1, about 25:1, about 30:1, about 35:1, about 40:1, about 45:1, or about 50:1. In one embodiment, the ratio of DGLA (or 15-OHEPA or 15-HETrE) to silica/charcoal is about 1:1 to about 50:1, for example about 1:1, about 2:1, about 3:1, about 4:1, about 5:1, about 6:1, about 7:1, about 8:1, about 9:1, about 10:1, about 12:1, about 14:1, about 15:1, about 16:1, about 18:1, about 20:1, about 25:1, about 30:1, about 35:1, about 40:1, about 45:1, or about 50:1. In one embodiment, crude DGLA, 15-OHEPA, and/or 15-HETrE has been deodorized by filtering over a CELITE filter. In another embodiment, lecithin is used in the deodorizing of the fatty acids.

In various embodiments, the invention provides pharmaceutical compositions, for example topically deliverable compositions, comprising one or more of DGLA, 15-OHEPA, 15-HETrE or mixtures thereof.

In one embodiment, the present disclosure provides pharmaceutical compositions comprising, for example, an amount (e.g., a therapeutically effective amount) of DGLA, 15-OHEPA, 15-HETrE, or a combination thereof. In one embodiment, the pharmaceutical composition comprises about 0.01 wt. % to about 50 wt. % of the DGLA, 15-OHEPA, 15-HETrE, or a combination thereof, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, about 10.1 wt. %, about 10.2 wt. %, about 10.3 wt. %, about 10.4 wt. %, about 10.5 wt. %, about 10.6 wt. %, about 10.7 wt. %, about 10.8 wt. %, about 10.9 wt. %, about 11 wt. %, about 11.1 wt. %, about 11.2 wt. %, about 11.3 wt. %, about 11.4 wt. %, about 11.5 wt. %, about 11.6 wt. %, about 11.7 wt. %, about 11.8 wt. %, about 11.9 wt. %, about 12 wt. %, about 12.1 wt. %, about 12.2 wt. %, about 12.3 wt. %, about 12.4 wt. %, about 12.5 wt. %, about 12.6 wt. %, about 12.7 wt. %, about 12.8 wt. %, about 12.9 wt. %, about 13 wt. %, about 13.1 wt. %, about 13.2 wt. %, about 13.3 wt. %, about 13.4 wt. %, about 13.5 wt. %, about 13.6 wt. %, about 13.7 wt. %, about 13.8 wt. %, about 13.9 wt. %, about 14 wt. %, about 14.1 wt. %, about 14.2 wt. %, about 14.3 wt. %, about 14.4 wt. %, about 14.5 wt. %, about 14.6 wt. %, about 14.7 wt. %, about 14.8 wt. %, about 14.9 wt. %, about 15 wt. %, about 15.1 wt. %, about 15.2 wt. %, about 15.3 wt. %, about 15.4 wt. %, about 15.5 wt. %, about 15.6 wt. %, about 15.7 wt. %, about 15.8 wt. %, about 15.9 wt. %, about 16 wt. %, about 16.1 wt. %, about 16.2 wt. %, about 16.3 wt. %, about 16.4 wt. %, about 16.5 wt. %, about 16.6 wt. %, about 16.7 wt. %, about 16.8 wt. %, about 16.9 wt. %, about 17 wt. %, about 17.1 wt. %, about 17.2 wt. %, about 17.3 wt. %, about 17.4 wt. %, about 17.5 wt. %, about 17.6 wt. %, about 17.7 wt. %, about 17.8 wt. %, about 17.9 wt. %, about 18 wt. %, about 18.1 wt. %, about 18.2 wt. %, about 18.3 wt. %, about 18.4 wt. %, about 18.5 wt. %, about 18.6 wt. %, about 18.7 wt. %, about 18.8 wt.%, about 18.9 wt. %, about 19 wt. %, about 19.1 wt. %, about 19.2 wt. %, about 19.3 wt. %, about 19.4 wt. %, about 19.5 wt. %, about 19.6 wt. %, about 19.7 wt. %, about 19.8 wt. %, about 19.9 wt. %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, or about 50 wt % of the DGLA, 15-OHEPA, 15-HETrE, or a combination thereof.

In one embodiment, the pharmaceutical composition further comprises an additional active agent. In one embodiment, the pharmaceutical composition comprises an amount of the additional active agent that is less than the generally recognized therapeutically effective amount for that agent. In one embodiment, the pharmaceutical composition comprises an amount of the additional active agent that is equal to or greater than the generally recognized therapeutically effective amount for that agent.

Any pharmaceutically acceptable excipient known to those of skill in the art may be used in pharmaceutical compositions according to the present disclosure. Any excipient selected for use in the therapeutic and cosmetic compositions should be pharmaceutically and/or cosmetically acceptable and appropriate for the form in which the therapeutic composition will be used, e.g., cream, gel, milk, oil, lotion, and the like. Preferably, the excipient has an affinity for the skin, is well tolerated, and stable when used in an amount adequate to provide the desired consistency and ease of application. By way of example only, a pharmaceutical composition according to the present disclosure may comprise one or more of: surfactants, preservatives, flavouring agents, co-solvents, viscosity aids, suspension aids, and lipophilic phases.

In one embodiment, the pharmaceutical composition comprises about 0.5 wt. % to about 5 wt. % of a surfactant such as an ethoxylated natural fatty alcohol (e.g., Steareth-2), for example, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, about 1.5 wt. %, about 1.55 wt. %, about 1.6 wt. %, about 1.65 wt. %, about 1.7 wt. %, about 1.75 wt. %, about 1.8 wt. %, about 1.85 wt. %, about 1.9 wt. %, about 1.95 wt. %, about 2 wt. %, about 2.05 wt. %, about 2.1 wt. %, about 2.15 wt. %, about 2.2 wt. %, about 2.25 wt. %, about 2.3 wt. %, about 2.35 wt. %, about 2.4 wt. %, about 2.45 wt. %, about 2.5 wt. %, about 2.55 wt. %, about 2.6 wt. %, about 2.65 wt. %, about 2.7 wt. %, about 2.75 wt. %, about 2.8 wt. %, about 2.85 wt. %, about 2.9 wt. %, about 2.95 wt. %, about 3 wt. %, about 3.05 wt. %, about 3.1 wt. %, about 3.15 wt. %, about 3.2 wt. %, about 3.25 wt. %, about 3.3 wt. %, about 3.35 wt. %, about 3.4 wt. %, about 3.45 wt. %, about 3.5 wt. %, about 3.55 wt. %, about 3.6 wt. %, about 3.65 wt. %, about 3.7 wt. %, about 3.75 wt. %, about 3.8 wt. %, about 3.85 wt. %, about 3.9 wt. %, about 3.95 wt. %, about 4 wt. %, about 4.05 wt. %, about 4.1 wt. %, about 4.15 wt. %, about 4.2 wt. %, about 4.25 wt. %, about 4.3 wt. %, about 4.35 wt. %, about 4.4 wt. %, about 4.45 wt. %, about 4.5 wt. %, about 4.55 wt. %, about 4.6 wt. %, about 4.65 wt. %, about 4.7 wt. %, about 4.75 wt. %, about 4.8 wt. %, about 4.85 wt. %, about 4.9 wt. %, about 4.95 wt. %, about 5 wt. % of the surfactant. In one embodiment the surfactant is Steareth-2 (e.g., BRIJ S2, Croda International plc).

In one embodiment, the pharmaceutical composition comprises about 0.5 wt. % to about 5 wt. % of an emulsifier such as a polyoxyethylene fatty ether (e.g., Steareth-21), for example, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, about 1.5 wt. %, about 1.55 wt. %, about 1.6 wt. %, about 1.65 wt. %, about 1.7 wt. %, about 1.75 wt. %, about 1.8 wt. %, about 1.85 wt. %, about 1.9 wt. %, about 1.95 wt. %, about 2 wt. %, about 2.05 wt. %, about 2.1 wt. %, about 2.15 wt. %, about 2.2 wt. %, about 2.25 wt. %, about 2.3 wt. %, about 2.35 wt. %, about 2.4 wt. %, about 2.45 wt. %, about 2.5 wt. %, about 2.55 wt. %, about 2.6 wt. %, about 2.65 wt. %, about 2.7 wt. %, about 2.75 wt. %, about 2.8 wt. %, about 2.85 wt. %, about 2.9 wt. %, about 2.95 wt. %, about 3 wt. %, about 3.05 wt. %, about 3.1 wt. %, about 3.15 wt. %, about 3.2 wt. %, about 3.25 wt. %, about 3.3 wt. %, about 3.35 wt. %, about 3.4 wt. %, about 3.45 wt. %, about 3.5 wt. %, about 3.55 wt. %, about 3.6 wt. %, about 3.65 wt. %, about 3.7 wt. %, about 3.75 wt. %, about 3.8 wt. %, about 3.85 wt. %, about 3.9 wt. %, about 3.95 wt. %, about 4 wt. %, about 4.05 wt. %, about 4.1 wt. %, about 4.15 wt. %, about 4.2 wt. %, about 4.25 wt. %, about 4.3 wt. %, about 4.35 wt. %, about 4.4 wt. %, about 4.45 wt. %, about 4.5 wt. %, about 4.55 wt. %, about 4.6 wt. %, about 4.65 wt. %, about 4.7 wt. %, about 4.75 wt. %, about 4.8 wt. %, about 4.85 wt. %, about 4.9 wt. %, about 4.95 wt. %, about 5 wt. % of the emulsifier. In one embodiment the emulsifier is Steareth-21 (e.g., BRIJ S721, Croda International plc).

In one embodiment, the pharmaceutical composition comprises a stabilizer such as a cetyl alcohol or a saturated cetyl alcohol (e.g., cetyl alcohol). In one embodiment, the pharmaceutical composition comprises about 0.1 wt. % to about 5 wt. % of a stabilizer, for example about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.01 wt. %, about 1.02 wt. %, about 1.03 wt. %, about 1.04 wt. %, about 1.05 wt. %, about 1.06 wt. %, about 1.07 wt. %, about 1.08 wt. %, about 1.09 wt. %, about 1.1 wt. %, about 1.11 wt. %, about 1.12 wt. %, about 1.13 wt. %, about 1.14 wt. %, about 1.15 wt. %, about 1.16 wt. %, about 1.17 wt. %, about 1.18 wt. %, about 1.19 wt. %, about 1.2 wt. %, about 1.21 wt. %, about 1.22 wt. %, about 1.23 wt. %, about 1.24 wt. %, about 1.25 wt. %, about 1.26 wt. %, about 1.27 wt. %, about 1.28 wt. %, about 1.29 wt. %, about 1.3 wt. %, about 1.31 wt. %, about 1.32 wt. %, about 1.33 wt. %, about 1.34 wt. %, about 1.35 wt. %, about 1.36 wt. %, about 1.37 wt. %, about 1.38 wt. %, about 1.39 wt. %, about 1.4 wt. %, about 1.41 wt. %, about 1.42 wt. %, about 1.43 wt. %, about 1.44 wt. %, about 1.45 wt. %, about 1.46 wt. %, about 1.47 wt. %, about 1.48 wt. %, about 1.49 wt. %, about 1.5 wt. %, about 1.51 wt. %, about 1.52 wt. %, about 1.53 wt. %, about 1.54 wt. %, about 1.55 wt. %, about 1.56 wt. %, about 1.57 wt. %, about 1.58 wt. %, about 1.59 wt. %, about 1.6 wt. %, about 1.61 wt. %, about 1.62 wt. %, about 1.63 wt. %, about 1.64 wt. %, about 1.65 wt. %, about 1.66 wt. %, about 1.67 wt. %, about 1.68 wt. %, about 1.69 wt. %, about 1.7 wt. %, about 1.71 wt. %, about 1.72 wt. %, about 1.73 wt. %, about 1.74 wt. %, about 1.75 wt. %, about 1.76 wt. %, about 1.77 wt. %, about 1.78 wt. %, about 1.79 wt. %, about 1.8 wt. %, about 1.81 wt. %, about 1.82 wt. %, about 1.83 wt. %, about 1.84 wt. %, about 1.85 wt. %, about 1.86 wt. %, about 1.87 wt. %, about 1.88 wt. %, about 1.89 wt. %, about 1.9 wt. %, about 1.91 wt. %, about 1.92 wt. %, about 1.93 wt. %, about 1.94 wt. %, about 1.95 wt. %, about 1.96 wt. %, about 1.97 wt. %, about 1.98 wt. %, about 1.99 wt. %, about 2 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt % of the stabilizer. In one embodiment, the stabilizer is cetyl alcohol (e.g., Crodacol C95 EP, Croda International plc).

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, niacinamide, and the like. In one embodiment, the pharmaceutical composition comprises about 0.01 wt. % to about 2 wt. % of an antioxidant, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

In one embodiment the antioxidant is ascorbyl palmitate. In one embodiment the antioxidant is α-tocopherol. In one embodiment the antioxidant is ascorbic acid. In one embodiment the antioxidant is idebenone. In one embodiment, the antioxidant is ubiquinone. In one embodiment, the antioxidant is ferulic acid. In one embodiment, the antioxidant is coenzyme Q10. In one embodiment, the antioxidant is lycopene. In one embodiment, the antioxidant is green tea. In one embodiment, the antioxidant is catechins. In one embodiment, the antioxidant is epigallocatechin 3-gallate (EGCG). In one embodiment, the antioxidant is green tea polyphenols (GTP). In one embodiment, the antioxidant is silymarin. In one embodiment, the antioxidant is coffeeberry. In one embodiment, the antioxidant is resveratrol. In one embodiment, the antioxidant is grape seed. In one embodiment, the antioxidant is pomegranate extracts. In one embodiment, the antioxidant is genisten. In one embodiment, the antioxidant is pycnogenol. In one embodiment, the antioxidant is niacinamide. In one embodiment, the pharmaceutical composition comprises about 0.01 wt. % to about 0.5 wt. % of one or more antioxidants selected from the group consisting of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide. In one embodiment, the pharmaceutical composition comprises about 0.1 wt. % to about 0.3 wt. % of one or more antioxidants selected from the group consisting of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide. In one embodiment, the pharmaceutical composition comprises about 0.3 wt. % to about 0.5 wt. % of one or more antioxidants selected from the group consisting of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide. In one embodiment, the pharmaceutical composition comprises about 0.45 wt. % of one or more antioxidants selected from the group consisting of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide. In one embodiment, the pharmaceutical composition comprises about 0.05 wt. % of idebenone. In one embodiment, the pharmaceutical composition comprises about 0.05 wt. % to about 1 wt. % of ubiquinone, for example about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt %, about 0.9 wt. %, about 0.95 wt. %, or about 1 wt. % of ubiquinone. In one embodiment, the pharmaceutical composition comprises about 0.1 wt. % to about 1 wt. % of ferulic acid, for example about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, or about 1 wt. % of ferulic acid. In one embodiment, the pharmaceutical composition comprises about 0.01 wt. % to about 0.5 wt. % of ascorbyl palmitate, about 0.01 wt. % to about 0.5 wt. % of α-tocopherol, and about 0.01 wt. % to about 0.5 wt. % of ascorbic acid. In one embodiment the pharmaceutical composition comprises about 0.1 wt. % to about 0.3 wt. % of ascorbyl palmitate, about 0.1 wt. % to about 0.3 wt. % of α-tocopherol, and about 0.05 wt. % to about 0.2 wt. % of ascorbic acid. In one embodiment the pharmaceutical composition comprises about 0.2 wt. % of ascorbyl palmitate, about 0.15 wt. % of α-tocopherol, and about 0.1 wt. % of ascorbic acid.

In one embodiment, the pharmaceutical composition comprises one or more emollients such as a fully saturated triglyceride (e.g., medium-chain triglycerides such as Crodamol GTCC, Croda International plc), myristyl myristate, isopropryl palmitate, and glycerin. In one embodiment, the pharmaceutical composition comprises about 0.5 wt. % to about 20 wt. % of an emollient, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, about 10.1 wt. %, about 10.2 wt. %, about 10.3 wt. %, about 10.4 wt. %, about 10.5 wt. %, about 10.6 wt. %, about 10.7 wt. %, about 10.8 wt. %, about 10.9 wt. %, about 11 wt. %, about 11.1 wt. %, about 11.2 wt. %, about 11.3 wt. %, about 11.4 wt. %, about 11.5 wt. %, about 11.6 wt. %, about 11.7 wt. %, about 11.8 wt. %, about 11.9 wt. %, about 12 wt. %, about 12.1 wt. %, about 12.2 wt. %, about 12.3 wt. %, about 12.4 wt. %, about 12.5 wt. %, about 12.6 wt. %, about 12.7 wt. %, about 12.8 wt. %, about 12.9 wt. %, about 13 wt. %, about 13.1 wt. %, about 13.2 wt. %, about 13.3 wt. %, about 13.4 wt. %, about 13.5 wt. %, about 13.6 wt. %, about 13.7 wt. %, about 13.8 wt. %, about 13.9 wt. %, about 14 wt. %, about 14.1 wt. %, about 14.2 wt. %, about 14.3 wt. %, about 14.4 wt. %, about 14.5 wt. %, about 14.6 wt. %, about 14.7 wt. %, about 14.8 wt. %, about 14.9 wt. %, about 15 wt. %, about 15.1 wt. %, about 15.2 wt. %, about 15.3 wt. %, about 15.4 wt. %, about 15.5 wt. %, about 15.6 wt. %, about 15.7 wt. %, about 15.8 wt. %, about 15.9 wt. %, about 16 wt. %, about 16.1 wt. %, about 16.2 wt. %, about 16.3 wt. %, about 16.4 wt.

%, about 16.5 wt. %, about 16.6 wt. %, about 16.7 wt. %, about 16.8 wt. %, about 16.9 wt. %, about 17 wt. %, about 17.1 wt. %, about 17.2 wt. %, about 17.3 wt. %, about 17.4 wt. %, about 17.5 wt. %, about 17.6 wt. %, about 17.7 wt. %, about 17.8 wt. %, about 17.9 wt. %, about 18 wt. %, about 18.1 wt. %, about 18.2 wt. %, about 18.3 wt. %, about 18.4 wt. %, about 18.5 wt. %, about 18.6 wt. %, about 18.7 wt. %, about 18.8 wt. %, about 18.9 wt. %, about 19 wt. %, about 19.1 wt. %, about 19.2 wt. %, about 19.3 wt. %, about 19.4 wt. %, about 19.5 wt. %, about 19.6 wt. %, about 19.7 wt. %, about 19.8 wt. %, about 19.9 wt. %, or about 20 wt. % of an emollient. In one embodiment, the pharmaceutical composition comprises about 0.5 wt. % to about 5 wt. % of any one emollient. In one embodiment, the one or more emollients are selected from the group consisting of medium-chain triglycerides (e.g., Crodamol GTCC, Croda International plc), myristyl myristate, isopropryl palmitate, and glycerin.

In one embodiment, the pharmaceutical composition comprises medium-chain triglycerides (e.g., Crodamol GTCC), myristyl myristate, isopropryl palmitate and glycerin in a combined amount of about 0.5 wt. to about 20 wt. %. In one embodiment, the pharmaceutical composition comprises about 0.5 wt. % to about 5 wt. % of medium-chain triglycerides (e.g., Crodamol GTCC), for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of medium-chain triglycerides (e.g., Crodamol GTCC). In one embodiment, the pharmaceutical composition comprises about 0.5 wt. % to about 5 wt. % of myristyl myristate, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of myristyl myristate.

In one embodiment, the pharmaceutical composition comprises about 0.5 wt. % to about 8 wt. % of isopropryl palmitate, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, or about 8 wt. % of isopropryl palmitate.

In one embodiment, the pharmaceutical composition comprises about 0.5 wt. % to about 5 wt. % of glycerin, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of glycerin. in one embodiment, the pharmaceutical composition comprises about 2 wt. % of medium-chain triglycerides (e.g., Crodamol GTCC), about 2 wt. % of myristyl myristate (e.g., Crodamol MM, Croda International plc), about 4 wt. % of isopropryl palmitate (e.g., Crodamol L IPP, Croda International plc), and about 1 wt. % of glycerin.

In one embodiment, the pharmaceutical composition comprises a preservative such as phenoxyethanol. In one embodiment, the pharmaceutical composition comprises about 0.1 wt. % to about 5 wt. % of a preservative, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of a preservative. In one embodiment, the preservative is phenoxyethanol. In one embodiment, the pharmaceutical composition comprises about 0.5 wt. % to about 5 wt. % of phenoxyethanol. In one embodiment, the pharmaceutical composition comprises about 0.5 wt. % to about 2 wt. % of phenoxyethanol. In one embodiment, the pharmaceutical composition comprises about 1 wt. % of phenoxyethanol.

In one embodiment, the pharmaceutical composition comprises one or more thickeners, such as a cross-linked polymer (e.g., a cross-linked acrylic acid polymer such as carbomer, available commercially as Carbopol ETD2020NF, Lubrizol Corp.), a polysaccharide (e.g., a xanthan gum such as CPKelko's Keltrol 11K). In one embodiment, the pharmaceutical composition comprises about 0.1 wt. % to about 5 wt. % of one or more thickeners, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of one or more thickeners. In one embodiment, the one or more thickeners is one or more of a cross-linked acrylic acid polymer and a polysaccharide. In one embodiment, the one or more thickeners are Carbopol ETD2020NF and Keltrol 11K. In one embodiment, the pharmaceutical composition comprises about 0.1 wt. % to about 5 wt. % of Carbopol ETD2020NF and about 0.1 wt. % to about 5 wt. % of Keltrol 11K. In one embodiment, the pharmaceutical composition comprises about 0.5 wt. % to about 1 wt. % of Carbopol ETD2020NF and about 0.2 wt. % to about 1 wt. % of Keltrol 11K. In one embodiment, the pharmaceutical composition comprises about 0.8 wt. % of Carbopol ETD2020NF and about 0.4 wt. % of Keltrol 11K.

In one embodiment, the pharmaceutical composition comprises one or more texturizers such as a lecithin (e.g., a liquid soy lecithin such as Leciprime 1400 IPM, Cargill, Inc.). In one embodiment, the pharmaceutical composition comprises about 0.1 wt. % to about 5 wt. % of one or more texturizers, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of one or more texturizers. In one embodiment, the one or more texturizers comprise Leciprime 1400 IPM. In one embodiment, the pharmaceutical composition comprises about 0.1 wt. % to about 5 wt. % of Lecirime 1400 IPM. In one embodiment, the pharmaceutical composition comprises about 0.2 wt. % to about 1 wt. % of Leciprime 1400 IPM. In one embodiment, the pharmaceutical composition comprises about 0.5 wt. % of Leciprime 1400 IPM.

In one embodiment, the pharmaceutical composition comprises one or more fragrances such as Floral Spa 760, Sensual Wood 138 or Mild Care 345. In one embodiment, the pharmaceutical composition comprises about 0.01 wt. % to about 0.5 wt. % of one or more fragrances, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, or about 0.5 wt. % of one or more fragrances. In one embodiment, the pharmaceutical composition comprises about 0.01 wt. % to about 0.5 wt. % of Mild Care 345 fragrance. In one embodiment, the pharmaceutical composition comprises about 0.01 wt. % to about 0.1 wt. % of Mild Care 345 fragrance. In one embodiment, the pharmaceutical composition comprises about 0.01 wt. % to about 0.05 wt. % of Mild Care 345 fragrance. In one embodiment, the pharmaceutical composition comprises about 0.05 wt. % of Mild Care 345 fragrance.

In one embodiment, the pharmaceutical composition comprises: about 0.1 wt. % DGLA to about 20 wt. % DGLA; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 0.1 wt. % DGLA to about 20 wt. % DGLA; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropryl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 0.1 wt. % DGLA to about 20 wt. % DGLA; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345.

In one embodiment, the pharmaceutical composition comprises: about 0.1 wt % DGLA to about 20 wt. % DGLA; optionally about 1.25 wt. % to about 10 wt. % of a sunscreen active agent; about 0.5 wt. % to about 5 wt. % of BRIJ S2; about 0.5 wt. % to about 5 wt. % of BRIJ S721; about 0.1 wt. % to about 5 wt. % of Crodamol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance In one embodiment, the pharmaceutical composition comprises: about 10 wt. % DGLA; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 10 wt. % DGLA; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropryl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 10 wt. % DGLA; optionally about 1.25 wt. % to about 10 wt. % of a sunscreen active agent; about 0.5 wt. % to about 5 wt % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, $\alpha$-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345.

In one embodiment, the pharmaceutical composition comprises: about 10 wt. % DGLA; optionally about 1.25 wt. % to about 10 wt. % of a sunscreen active agent; about 0.5 wt. % to about 5 wt. % of BRIJ S2; about 0.5 wt. % to about 5 wt. % of BRIJ S721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance. In one embodiment, the pharmaceutical composition comprises: about 1 wt. % DGLA; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 1 wt. % DGLA; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropryl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 1 wt. % DGLA; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, $\alpha$-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345. In one embodiment, the pharmaceutical composition comprises: about 1 wt. % DGLA; optionally about 1.25 wt. % to about 10 wt. % of a sunscreen active agent; about 0.5 wt. % to about 5 wt. % of BRIJ S2; about 0.5 wt. % to about 5 wt. % of BRIJ S721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Lecirprime 1400 IPM; and about 0.01 wt. % to about 0.5 wt. % of Mild Care 345 fragrance In one embodiment, the pharmaceutical composition comprises: about 0.1 wt. % DGLA; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 0.1 wt. % DGLA; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropryl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 0.1 wt. % DGLA; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345.

In one embodiment, the pharmaceutical composition comprises: about 0.1 wt. % DGLA; optionally about 1.25 wt. % to about 10 wt. % of a sunscreen active agent; about 0.5 wt. % to about 5 wt. % of BRIJ S2; about 0.5 wt. % to about 5 wt. % of BRIJ S721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance In one embodiment, the pharmaceutical composition comprises: about 0.01 wt. % to about 50 wt. % 15-HETrE; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 0.01 wt. % to about 50 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropryl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 0.01 wt. % to about 50 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345.

In one embodiment, the pharmaceutical composition comprises: about 0.01 wt. % to about 50 wt. % 15-HETrE; optionally about 1.25 wt. % to about 10 wt. % of a sunscreen active agent; about 0.5 wt. % to about 5 wt. % of BRIJ S2; about 0.5 wt. % to about 5 wt. % of BRIJ S721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance In one embodiment, the pharmaceutical composition comprises: about 10 wt. % 15-HETrE; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 10 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropryl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt % of one or more fragrances.

In one embodiment, the pharmaceutical composition comprises: about 10 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345.

In one embodiment, the pharmaceutical composition comprises: about 10 wt. % 15-HETrE; optionally about 1.25 wt. % to about 10 wt. % of a sunscreen active agent; about 0.5 wt. % to about 5 wt. % of BRIJ S2; about 0.5 wt. % to about 5 wt % of BRIJ S721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance In one embodiment, the pharmaceutical composition comprises: about 1 wt. % 15-HETrE; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 1 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropyl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 1 wt. % 15-HETrE; optionally about 1.25 wt. % to about 10 wt. % of a sunscreen active agent; about 0.5 wt % to about 5 wt. % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345.

In one embodiment, the pharmaceutical composition comprises: about 1 wt. % 15-HETrE; optionally about 1.25 wt. % to about 10 wt. % of a sunscreen active agent; about 0.5 wt. % to about 5 wt. % of BRIJ S2; about 0.5 wt. % to about 5 wt. % of BRIJ S721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance In one embodiment, the pharmaceutical composition comprises: about 0.1 wt. % 15-HETrE; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 0.1 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropyl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 0.1 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345.

In one embodiment, the pharmaceutical composition comprises: about 0.1 wt. % 15-HETrE; optionally about 1.25 wt. % to about 10 wt. % of a sunscreen active agent; about 0.5 wt. % to about 5 wt. % of BRIJ S2; about 0.5 wt. % to about 5 wt. % of BRIJ S721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance In one embodiment, the pharmaceutical composition comprises: about 0.01 wt. % 15-HETrE; optionally about 1.25 wt. % to about 10 wt. % of a sunscreen active agent; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 0.01 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropryl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 0.01 wt. % 15-HETrE; optionally about 1.25 wt. % to about 10 wt. % of a sunscreen active agent; about 0.5 wt. % to about 5 wt. % of Steareth-2; about 0.5 wt. % to about 5 wt. % of Steareth-21; about 0.05 wt. % to about 5 wt. % of cetyl alcohol; about 0.01 wt. % to about 2 wt. % of a combination of one or more of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide; about 0.5 wt. % to about 20 wt. % of a combination of one or more of Crodamol GTCC, myristyl myristate, isopropyl palmitate, and glycerin; about 0.1 wt. % to about 5 wt. % of phenoxyethanol; about 0.1 wt. % to about 5 wt. % of a combination of one or more of cross-linked acrylic acid (e.g., Carbopol ETD2020NF), and polysaccharides (e.g., Keltrol 11K); about 0.1 wt. % to about 5 wt. % of lecithin; and about 0.01 wt. % to about 0.5 wt. % of a combination of one or more of Floral Spa 760, Sensual Wood 138, and Mild Care 345.

In one embodiment, the pharmaceutical composition comprises: about 0.01 wt. % 15-HETrE; optionally about 1.25 wt. % to about 10 wt. % of a sunscreen active agent; about 0.5 wt. % to about 5 wt. % of BRIJ S2; about 0.5 wt. % to about 5 wt. % of BRIJ S721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In one embodiment, a composition including, for example, a pharmaceutical composition, as disclosed herein is formulated as an aerosol, a gel, an ointment, a lotion, a cream, a gel stick, a liniment, or a spray.

Such formulations may be stable and comprise an amount (e.g., a therapeutically effective amount) of DGLA, 15-OHEPA, and//or 15-HETrE, optionally in combination with one or more sunscreen active agents.

The present disclosure also provides the disclosed compositions or formulations as a component in a product for use in the prevention and/or treatment of effects associated with UV radiation such as erythema. In one embodiment, the product comprises a container and a pharmaceutical composition comprising a therapeutically effective amount of DGLA, 15-OHEPA, and/or 15-HETrE, or a combination thereof, and optionally one or more sunscreen active agents.

Pharmacokinetics/Pharmacodynamics

The pharmacokinetics and/or pharmacodynamics of the compositions comprising DGLA, 15-OHEPA, or 15-HETrE as disclosed herein may be determined by any method known in the art.

In an embodiment, the pharmacokinetics of a composition comprising DGLA, 15-OHEPA, or 15-HETrE as disclosed herein may be examined using a skin blister technique (see, e.g., Tope, Dermatol Surg 25:348:52 (1999)) to determine the amount of various constituents of the composition that are absorbed through the skin. In an exemplary method, a defined area of the skin is contacted with one or more doses of the compositions at one or more time intervals. Next, epidermal blisters may be made by application of controlled suction to an area of the skin (see, e.g., Kiistala (1968) J. Investig. Dermatol. 50:129-137; Kiistala, et al. (1964) Lancet 1964: 1444-1445; and Schreiner, et al. (1978) Scand. J. Infect. Dis. 14(Suppl.):233-237). Prior to the start of forming a blister on an area of the skin, the area may be hydrated with a warm compress and/or swabbed with 70% isopropanol. Next, a suction apparatus may be placed on the area of the skin and controlled suction applied to with an electric vacuum pump. The vacuum may be increased slowly over a period of time (e.g., 1 min) up to a maximum negative pressure sufficient to form a blister (e.g., 0.3 kg/cm$^2$ (3.104 Pa)). The pressure may be maintained for several hours (e.g., 2 to 3 h) until hemispherical blisters are formed. As soon as the blisters appeared, the vacuum may be released, and the suction chamber apparatus carefully removed without breaking the blister. The blister fluid (e.g., 50-500 µL) may then be aspirated and examined. Samples of blister fluid may be stored at −70° C. until analysis. The concentration of DGLA, 15-OHEPA, or 15-HETrE or other constituents from the disclosed compositions may be determined in blister fluid samples by any method known in the art including, for example, gas chromatography MS (GC/MS), or reverse-phase high-performance liquid chromatography (HPLC).

In an embodiment, the pharmacokinetics of a composition comprising DGLA, 15-OHEPA, or 15-HETrE as disclosed herein may be examined using cutaneous microdialysis (see e.g. Salgo Experimental Dermatology 20:130-133 (2011)) to determine the amount of various constituents of the composition that are absorbed through the skin. In an exemplary method, a defined area of the skin is contacted with one or more doses of the compositions at one or more time intervals. Then, after placing an introducer cannule, two catheters with permeable membranes can be placed directly into the skin, one into the area treated, and one into non-treated skin. Catheters can then be flushed with a 1:1 mixture of isotonic sodium solution and Ringer's solution, using a CMA 402 syringe pump with a flow rate of 1 µl/min. Microdialysis can be performed continuously for prespecified lengths of time. Samples can be collected stored at −70° C. until they are used for analyses.

The compositions comprising DGLA as provided herein deliver DGLA at a mean flux rate of from about 0.1 ng to about 1 mg/cm$^2$/hr at about 2, 4, 6, 8, 12, 24, 48 or 72 hours after administration. The compositions comprising 15-OHEPA as provided herein deliver 15-OHEPA at a mean flux rate of from about 0.1 ng to about 1 mg/cm$^2$/hr at about 2, 4, 6, 8, 12, 24, 48 or 72 hours after administration. The compositions comprising 15-HETrE as provided herein deliver 15-HETrE at a mean flux rate of from about 0.1 ng to about 1 mg/cm$^2$/hr at about 2, 4, 6, 8, 12, 24, 48 or 72 hours after administration.

Methods of Treatment of Diseases and/or Disorders

The compositions and formulations disclosed herein may be used in the prevention and/or treatment of one or more effects associated with exposure to UV radiation including, for example, erythema or edema.

The present disclosure provides compositions, for preventing or reducing the occurrence of erythema, that comprise a therapeutically effective amount of DGLA, 15-OHEPA, and/or 15-HETrE. In some embodiments, the composition comprises about 0.1 wt. % DGLA to about 20 wt. % DGLA (e.g., about 10 wt. % DGLA, about 1.0 wt. % DGLA, or about 0.1 wt. % DGLA). In some embodiments, the composition comprises about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE). In some embodiments, the composition comprise about 0.1 wt. % DGLA to about 20 wt. % DGLA (e.g., about 10 wt. % DGLA, about 1.0 wt. % DGLA, or about 0.1 wt. % DGLA) and about 0.01 wt. % to about 50 wt. % 15-HETrE (e.g., 10 wt. % 15-HETrE, about 1.0 wt. % 15-HETrE, about 0.1 wt % 15-HETrE, or about 0.01 wt. % 15-HETrE)

The present disclosure also provides a photoprotective composition, for preventing or reducing the occurrence of erythema, that comprises i.) a therapeutically effective amount of DGLA and/or 15-HETrE; and ii.) a sunscreen active agent. In some embodiments, the composition comprises about 0.1 wt. % DGLA to about 20 wt. % DGLA (e.g., about 10 wt. % DGLA, about 1.0 wt. % DGLA, or about 0.1 wt. % DGLA). In some embodiments, the composition comprises about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE). In some embodiments, the composition comprise about 0.1 wt. % DGLA to about 20 wt. % DGLA (e.g., about 10 wt. % DGLA, about 1.0 wt. % DGLA, or about 0.1 wt. % DGLA) and about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE).

The present disclosure also provides methods for preventing or reducing the occurrence of erythema on at least one area of the skin of a subject, comprising: topically applying a therapeutically effective amount of a composition comprising DGLA or 15-HETrE to the at least one area of skin of the subject. In some embodiments, the composition comprises about 0.1 wt. % DGLA to about 20 wt. % DGLA (e.g., about 10 wt. % DGLA, about 1.0 wt. % DGLA, or about 0.1 wt. % DGLA). In some embodiments, the composition comprises about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE). In some embodiments, the composition comprise about 0.1 wt. % DGLA to about 20 wt. % DGLA (e.g., about 10 wt. % DGLA, about 1.0 wt. % DGLA, or about 0.1 wt. % DGLA) and about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE).

The present disclosure also provides methods for preventing or reducing sun-induced damage of the skin of a subject, comprising: topically applying the composition comprising DGLA or 15-HETrE to the at least one area of skin of the subject. In some embodiments, the composition comprises about 0.1 wt. % DGLA to about 20 wt. % DGLA (e.g., about 10 wt. % DGLA, about 1.0 wt. % DGLA, or about 0.1 wt. % DGLA). In some embodiments, the composition comprises about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE). In some embodiments, the composition comprise about 0.1 wt. % DGLA to about 20 wt. % DGLA (e.g., about 10 wt. % DGLA, about 1.0 wt. % DGLA, or about 0.1 wt. % DGLA) and about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE).

The present disclosure also provides methods for increasing the Sun Protection Factor (SPF) of a sunscreen, comprising: adding a composition comprising DGLA and/or 15-HETrE to the sunscreen. In some embodiments, the composition comprises about 0.1 wt. % DGLA to about 20 wt. % DGLA (e.g., about 10 wt. % DGLA, about 1.0 wt. % DGLA, or about 0.1 wt. % DGLA). In some embodiments, the composition comprises about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE). In some embodiments, the composition comprise about 0.1 wt. % DGLA to about 20 wt. % DGLA (e.g., about 10 wt. % DGLA, about 1.0 wt. % DGLA, or about 0.1 wt. % DGLA) and about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE).

The present disclosure also provides methods for preventing or reducing the deleterious effects of UV radiation that contacts a surface, comprising: applying to the surface a composition comprising DGLA and/or 15-HETrE. In some embodiments, the composition comprises about 0.1 wt. % DGLA to about 20 wt. % DGLA (e.g., about 10 wt. % DGLA, about 1.0 wt. % DGLA, or about 0.1 wt. % DGLA). In some embodiments, the composition comprises about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE). In some embodiments, the composition comprise about 0.1 wt. % DGLA to about 20 wt. % DGLA (e.g., about 10 wt. % DGLA, about 1.0 wt. % DGLA, or about 0.1 wt. % DGLA) and about 0.01 wt. % to about 50 wt. % 15-HETrE (e.g., 10 wt. % 15-HETrE, about 1.0 wt. % 15-HETrE, about 0.1 wt. % 15-HETrE, or about 0.01 wt. % 15-HETrE).

In one embodiment, the method comprises administering a pharmaceutical composition as disclosed herein once per day, twice per day, three times per day, or more than three times per day.

In one embodiment, upon treatment in accordance with the present disclosure, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the treated area of the skin comprises about 10%, about 20%, about 30%, about 40%, about 50%, about 60%, about 70%, about 80%, about 90%, or greater than about 90% reduction in Draize score (see, Table 2 below) as compared to skin that has not been treated.

As used herein, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Use of Compositions Comprising DGLA and/or 15-HETrE for the Treatment and/or Prevention of Edema and/or Erythema Compositions comprising DGLA and/or 15-HETrE were tested for their ability to treat and/or prevent edema and erythema (e.g., UV induced erythema). In an exemplary method, a Sinclair miniature swine model of phototoxicity testing was employed to examine the effects of such compositions on UV-induced edema and erythema. Miniature swine were chosen for these studies as they have a skin structure that closely resembles that of humans.

The miniature swine used in these studies were fed standard Sinclair S-9 ration or equivalent, once a day at a maintenance amount and had ad libitum access to deep well water. Throughout the study, the swine were housed individually in cages (~3×5 ft) constructed of stainless steel with self-spanned polyvinyl chloride (PVC)-coated expanded metal flooring. The animal housing rooms were set to maintain a room temperature of 16 to 27° C. (61 to 81° F.), with fluorescent lights providing an approximate 12-hr light/12-hr dark photoperiod. The animals were acclimated for approximately 5 days prior to the start of dosing. During acclimation, animals were subject to a physical examination by a veterinarian and any animal with questionable health was excluded from these studies.

For these studies, two groups each consisting of three animals (#1-#3) were used. For each animal, ten sites (e.g., dose sites) for were established on the torso and the hair at the site was clipped with an electric clipper. These sites were then shaved and demarcated by tattooing at least four days prior to the start of initial dosing on study day 1. The dose sites may be shaved with a razor the day prior to initial dose administration and prior to the second and third application when applicable. The sites (approximately 4 cm² in size) were evenly split on the left and right side with 5 sites demarcated on each side.

Each animal was topically administered a composition comprising a control vehicle (ethanol), DGLA or HETrE to the demarcated test sites on the animal before and/or after exposure of the test sites to UV radiation. Specifically, a 0.1 mL dose of a composition comprising 1 mg/mL, 10 mg/mL, or 100 mg/mL of DGLA and a 0.1 mL dose of a composition comprising 0.1 mg/mL, 1.0 mg/mL, or 10 mg/mL 15-HETrE was applied to separate 4 cm² areas of the skin (e.g., test sites) on each animal to achieve a dose per area of 0.1 mg/4 cm², 1.0 mg/4 cm², or 10.0 mg/4 cm² DGLA or 0.1 mg/4 cm², 1.0 mg/4 cm², or 10.0 mg/4 cm² 15-HETrE, respectively. Such compositions were applied via a pipette twice daily with approximately seven hours between administrations over 7 days. Table 1 below outlines the dosing regimen for the 10 sites on each animal and indicates the day that the animal was administered a dose of UV radiation. For example, for test sites 5-7, the sites were first exposed to UV radiation on day 4 and then contacted topically with DGLA or HETrE on days 4-10. Additionally, for example, for test sites 8-10, the sites were topically contacted with DGLA or HETrE on days 1-7 and then exposed to UV radiation on day 8.

TABLE 1

Dose Application Schedule

| Site Number | Duration of Exposure | DGLA, HETrE or Vehicle | Day of UV Dose Administration | DGLA, HETrE or Vehicle Admin. Study Days | Biopsy Collection |
|---|---|---|---|---|---|
| 6 | 7 days | Ethanol | NA | 5-11 | 12 |
| 1 | N/A | UV Light | 8 | NA | |
| 2 | 7 days | Ethanol + UV Light | 8 | 1-7 | |
| 7 | 7 days | UV Light + Ethanol | 4 | 4-10 | |
| 8 | 7 days | UV Light + DGLA or HETrE | 4 | 4-10 | |
| 9 | 7 days | UV Light + DGLA or HETrE | 4 | 4-10 | |
| 10 | 7 days | UV Light + DGLA or HETrE | 4 | 4-10 | |
| 3 | 7 days | DGLA or HETrE + UV Light | 8 | 1-7 | |
| 4 | 7 days | DGLA or HETrE + UV Light | 8 | 1-7 | |
| 5 | 7 days | DGLA or HETrE + UV Light | 8 | 1-7 | |

* For sites 4-7, the initial application of appropriate material will be ~15 minutes post completion of UV light application.

Animals receiving UV light were anesthetized via isoflurane gas and 100% oxygen. To expose the animals to UV, a bank of fluorescent lamps utilizing 10 UVA and 1 UVB bulb was then suspended over the animal. The correct dose level of UV light applied to the designated dose site was verified using a Solar Light® light meter. Animals were exposed to MED/hi of 4 for a time period of 21 minutes yielding a MEDi of 1.4. Skin that was not exposed to UV for the purposes of these studies was occluded using appropriate materials to prevent exposing areas outside the intended dose area.

The dose sites were observed for skin irritation at pre-dose and then 1 hour post dose administration on each dose administration day using a modified Draize scoring system detailed below in Table 2. All sites exposed to UV radiation also had Draize scoring performed at pre-dose, 1, 4, 12, 24, and 72 hours post UV exposure.

TABLE 2

Modified Draize Scoring System

| Category | Score | Description |
|---|---|---|
| Erythema | 0 | None |
| | 1 | Slight |
| | 2 | Well-defined |
| | 3 | Moderate or severe |
| | 4 | Severe or slight eschar formation (injuries in depth) |
| Edema | 0 | None |
| | 1 | Very slight |
| | 2 | Slight (well-defined edges) |
| | 3 | Moderate (raised >1 mm) |
| | 4 | Severe (raised >1 mm and extending beyond the area of exposure) |

Figure 2:
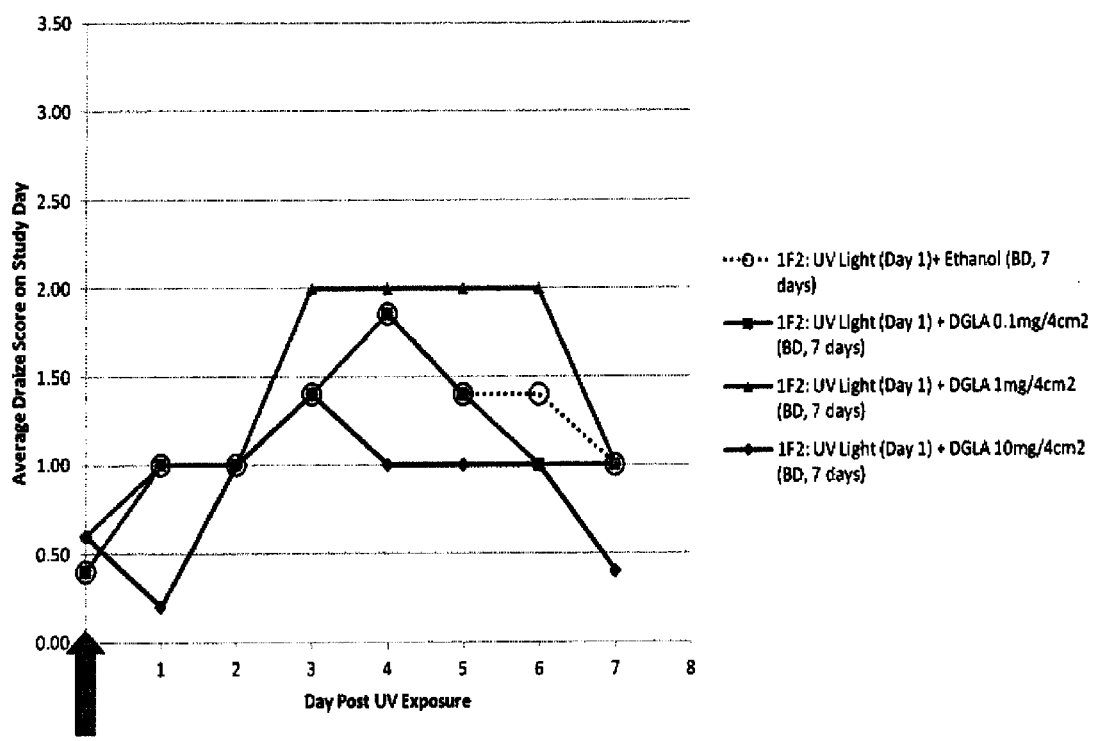
FIG. 2 shows a graphical representation of the average daily Draize score for selected areas of the skin of miniature swine #2 exposed to UV and then topically administered a composition comprising ethanol (vehicle), 1 mg/mL DGLA, 10 mg/mL DGLA, or 100 mg/mL DGLA twice daily for each of seven days.
Figure 3:
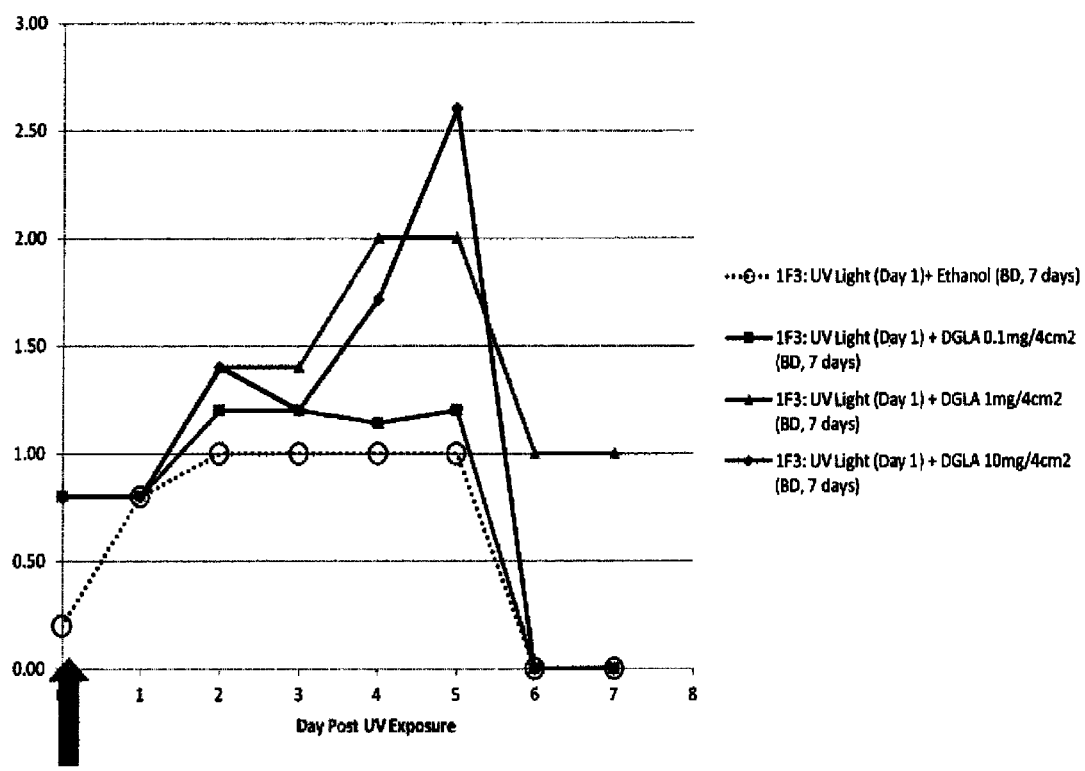
FIG. 3 shows a graphical representation of the average daily Draize score for selected areas of the skin of miniature swine #3 exposed to UV and then topically administered a composition comprising ethanol (vehicle), 1 mg/mL DGLA, 10 mg/mL DGLA, or 100 mg/mL DGLA twice daily for each of seven days.
Figure 4:
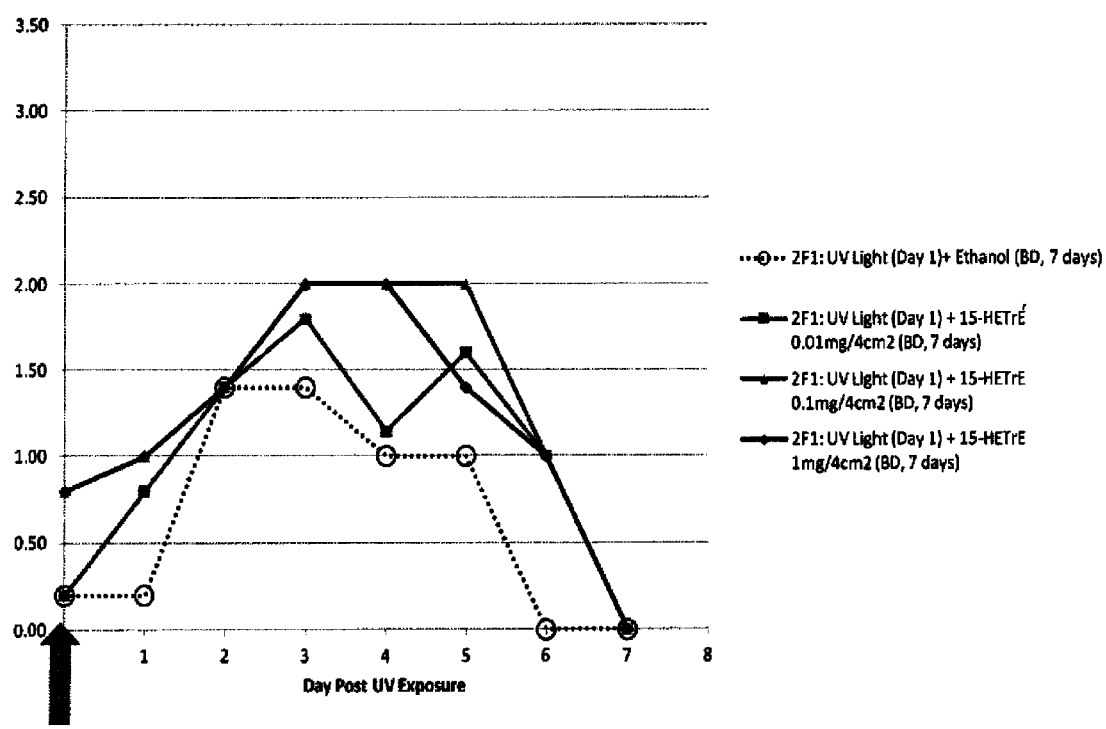
FIG. 4 shows a graphical representation of the average Draize score for selected areas of the skin of miniature swine #1 exposed to UV and then topically administered a composition comprising ethanol (vehicle), 0.1 mg/mL 15-HETrE, 1.0 mg/mL 15-HETrE, or 10.0 mg/mL 15-HETrE twice daily for each of seven days.
Figure 5:
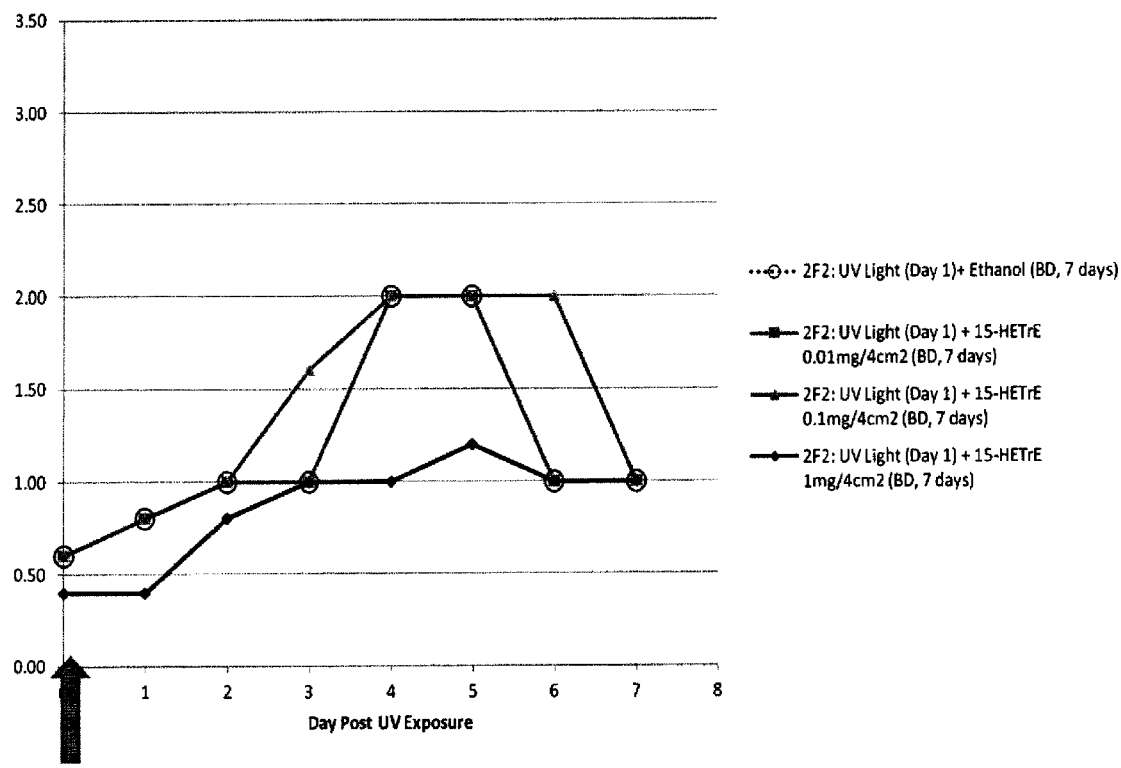
FIG. 5 shows a graphical representation of the average Draize score for selected areas of the skin of miniature swine #2 exposed to UV and then topically administered a composition comprising ethanol (vehicle), 0.1 mg/mL 15-HETrE, 1.0 mg/mL 15-HETrE, or 10.0 mg/mL 15-HETrE twice daily for each of seven days.
Figure 6:
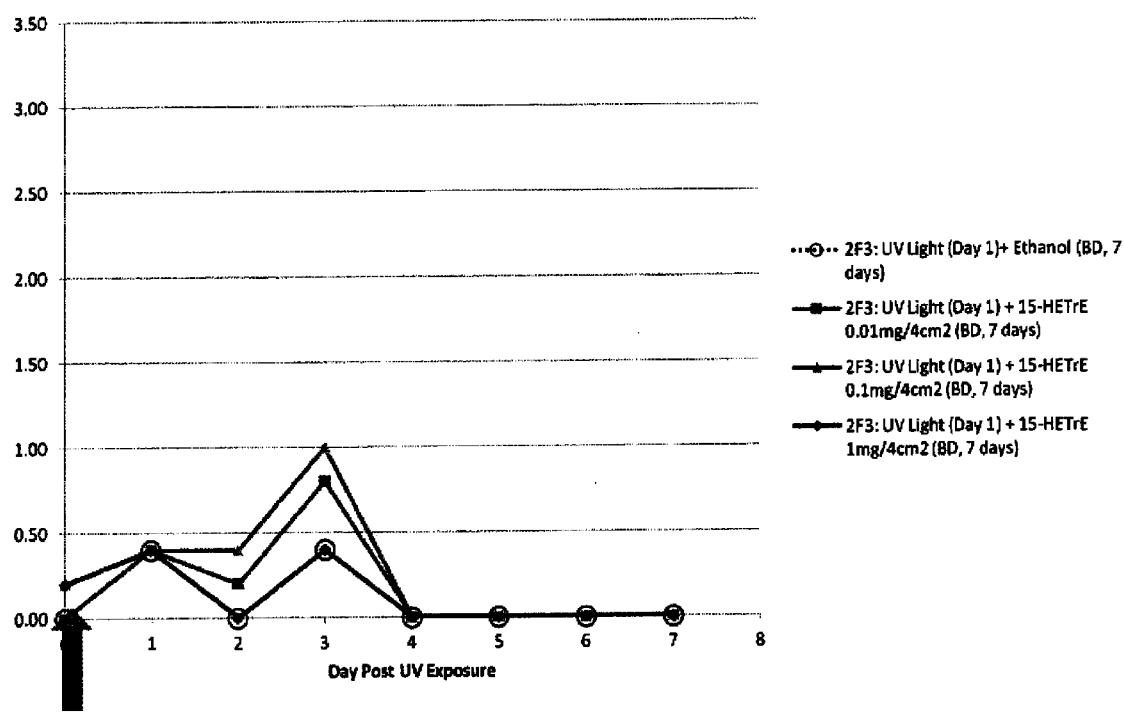
FIG. 6 shows a graphical representation of the average Draize score for selected areas of the skin of miniature swine #3 exposed to UV and then topically administered a composition comprising ethanol (vehicle), 0.1 mg/mL 15-HETrE, 1.0 mg/mL 15-HETrE, or 10.0 mg/mL 15-HETrE twice daily for each of seven days.
Figure 7:
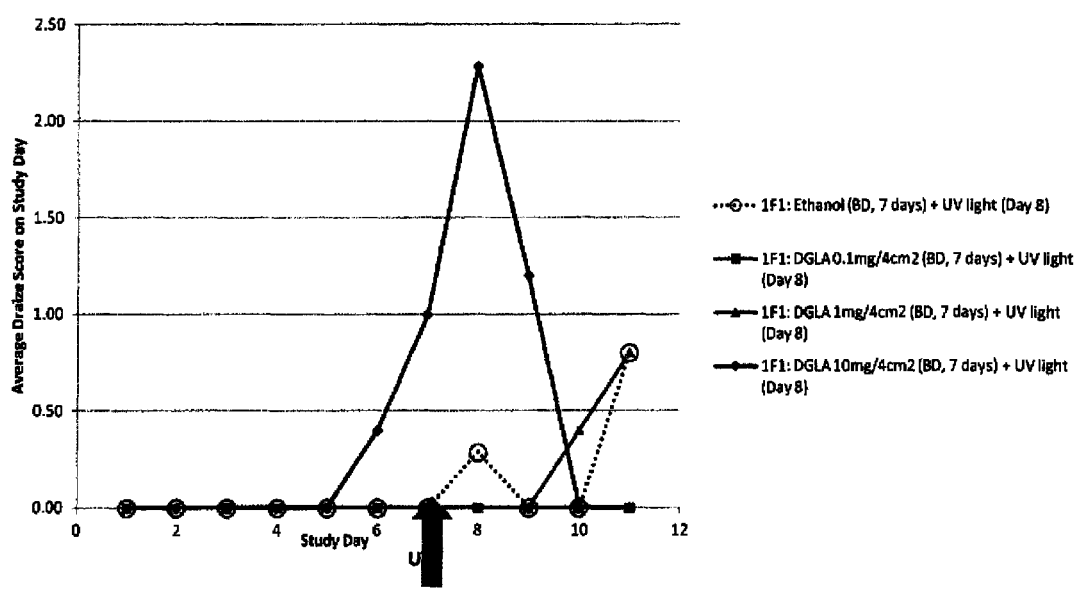
FIG. 7 shows a graphical representation of the average Draize score for selected areas of the skin of miniature swine #1 topically administered a composition comprising ethanol (vehicle), 1 mg/mL DGLA, 10 mg/mL DGLA, or 100 mg/mL DGLA twice daily for each of seven days and then exposed to UV.
Figure 8:
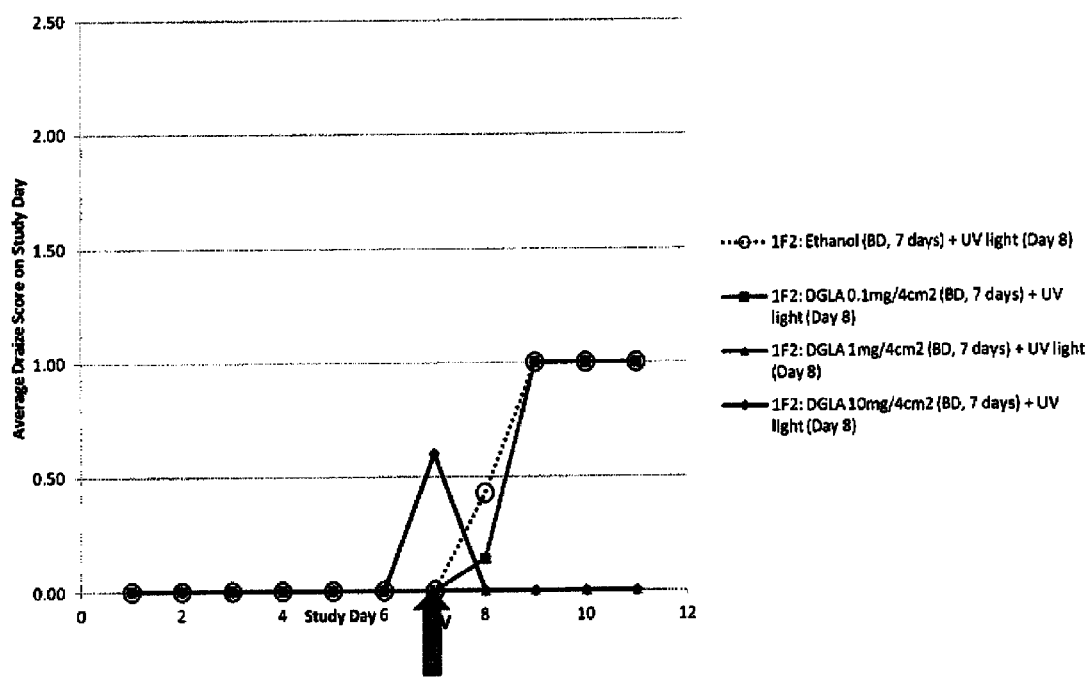
FIG. 8 shows a graphical representation of the average Draize score for selected areas of the skin of miniature swine #2 topically administered a composition comprising ethanol (vehicle), 1 mg/mL DGLA, 10 mg/mL DGLA, or 100 mg/mL DGLA twice daily for each of seven days and then exposed to UV.
Figure 9:
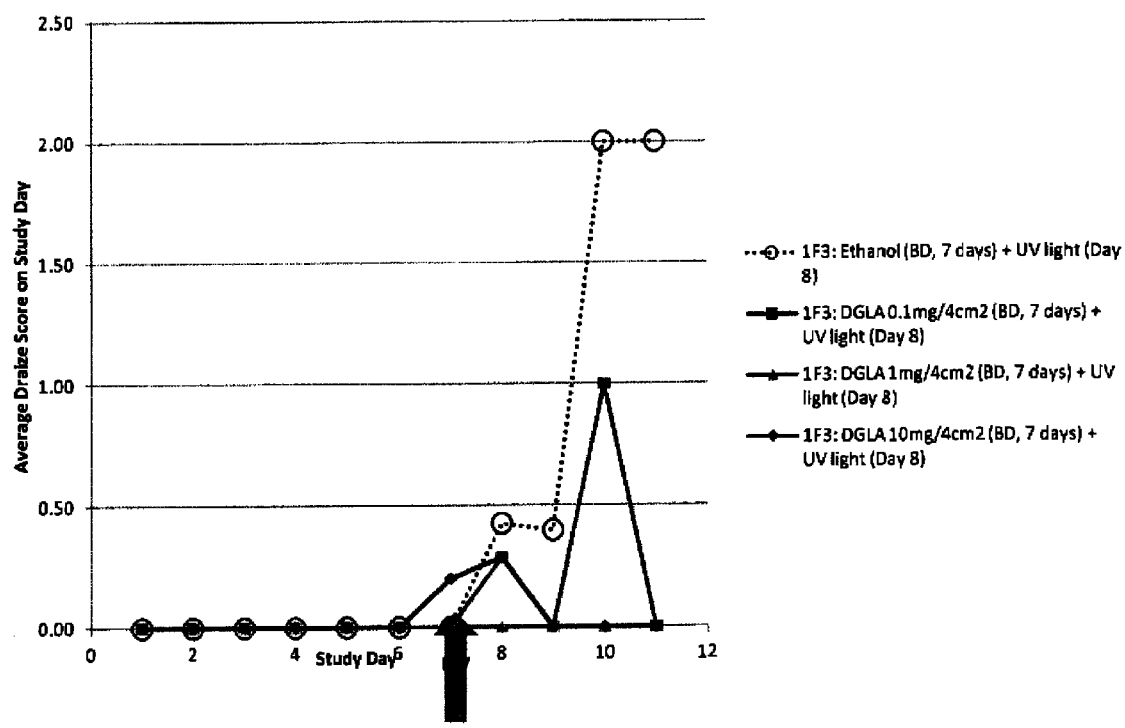
FIG. 9 shows a graphical representation of the average Draize score for selected areas of the skin of miniature swine #3 topically administered a composition comprising ethanol (vehicle), 1 mg/mL DGLA, 10 mg/mL DGLA, or 100 mg/mL DGLA twice daily for each of seven days and then exposed to UV.
Figure 10:
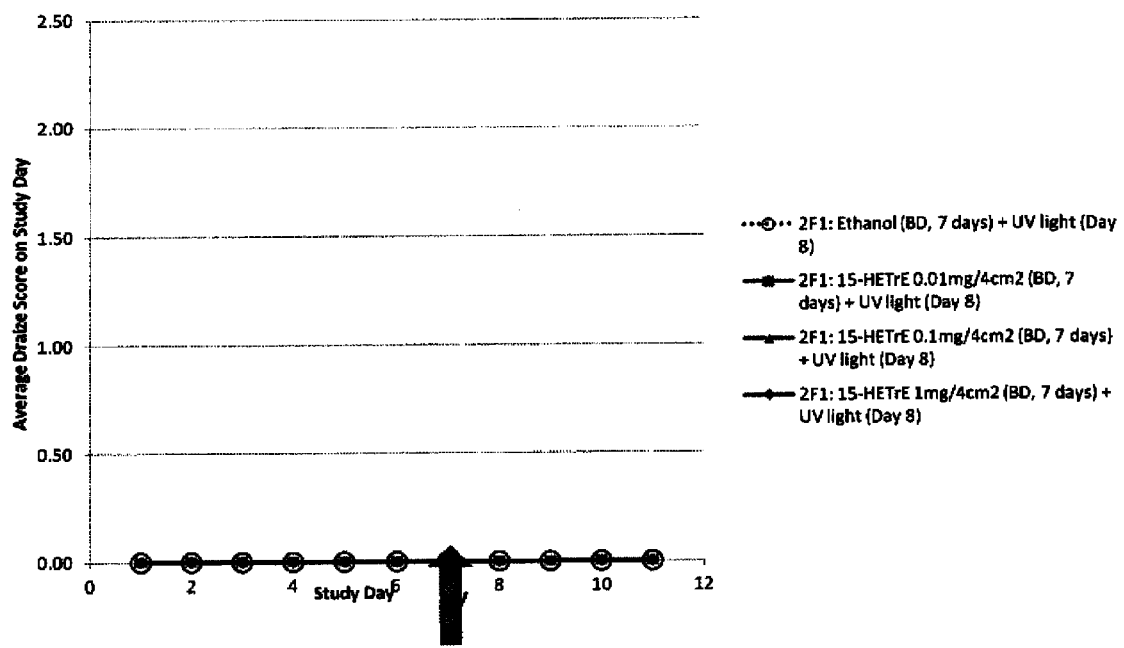
FIG. 10 shows a graphical representation of the average Draize score for selected areas of the skin of miniature swine #1 topically administered a composition comprising ethanol (vehicle), 0.1 mg/mL 15-HETrE, 1.0 mg/mL 15-HETrE, or 10.0 mg/mL 15-HETrE twice daily for each of seven days and then exposed to UV.
Figure 11:
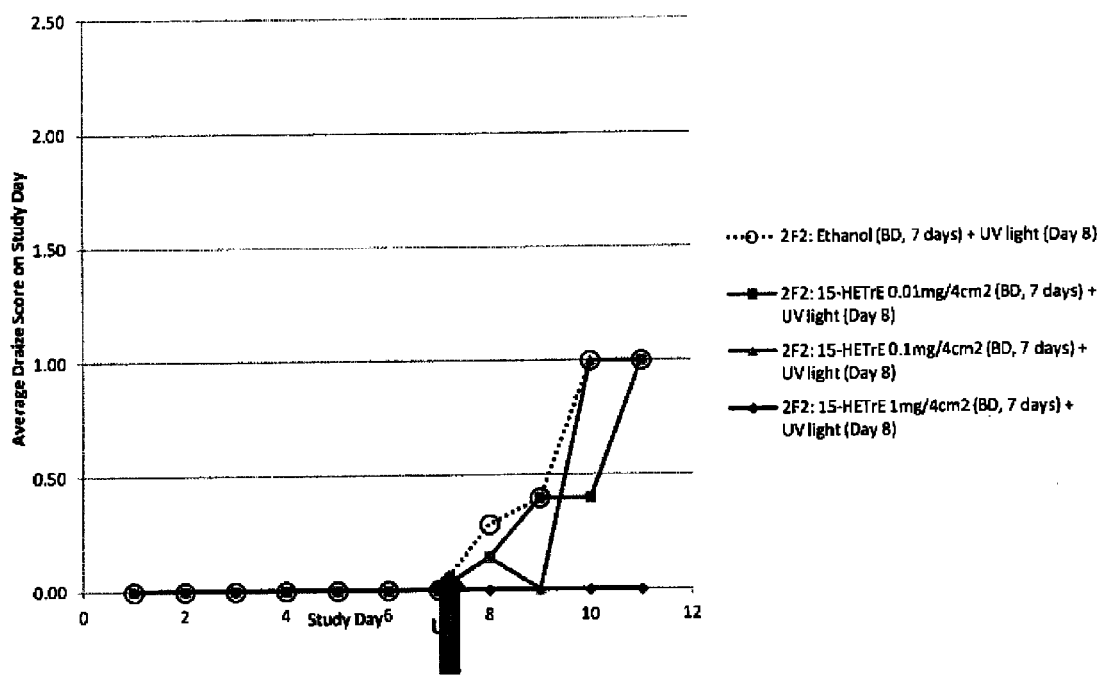
FIG. 11 shows a graphical representation of the average Draize score for selected areas of the skin of miniature swine #2 topically administered a composition comprising ethanol (vehicle), 0.1 mg/mL 15-HETrE, 1.0 mg/mL 15-HETrE, or 10.0 mg/mL 15-HETrE twice daily for each of seven days and then exposed to UV.
Figure 12:
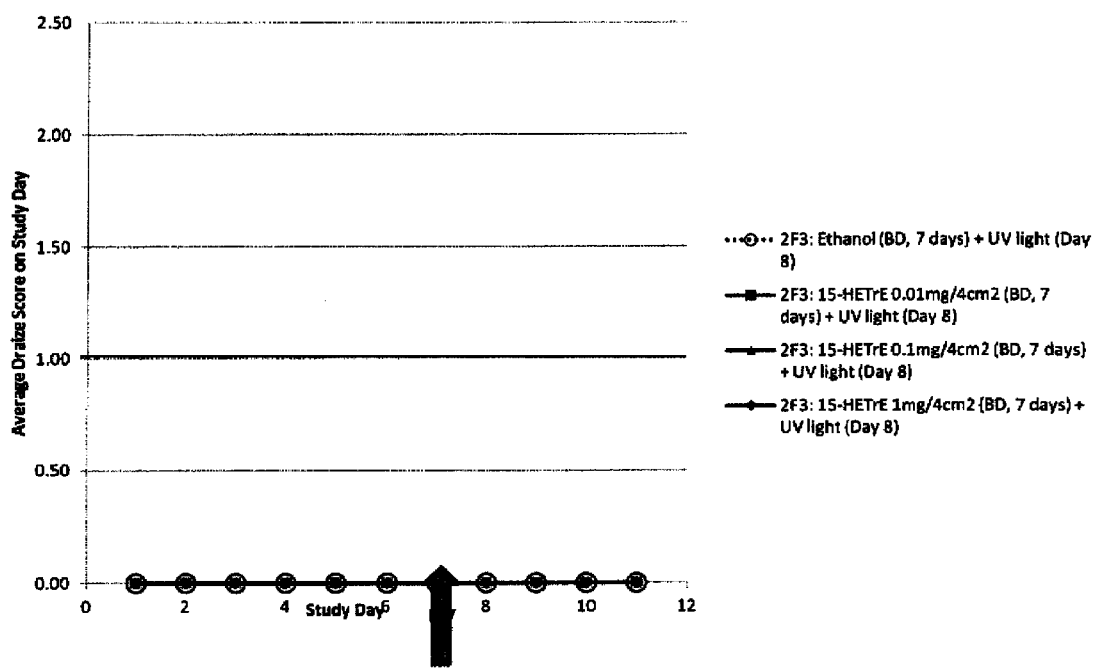
FIG. 12 shows a graphical representation of the average Draize score for selected areas of the skin of miniature swine #3 topically administered a composition comprising ethanol (vehicle), 0.1 mg/mL 15-HETrE, 1.0 mg/mL 15-HETrE, or 10.0 mg/mL 15-HETrE twice daily for each of seven days and then exposed to UV.

Test sites that were first exposed to UV radiation and then subsequently treated with a composition comprising any of the tested dosages of DGLA or HETrE did not exhibit an appreciable difference in average Draize score as compared to test sites treated with the control vehicle (see, FIGS. 1-6). However, those test sites that were first treated with DGLA or HETrE and then subsequently exposed to UV radiation demonstrated a significant reduction in their average Draize score as compared to test sites treated with the control vehicle (see, FIGS. 7-12). In particular, a dose of 0.1 or 1.0 mg/mL DGLA and a dose of 0.01, 0.1, or 1.0 mg/mL HETrE was able to prevent UV-induced erythema. However, it could not be determined if the 10 mg/mL dose of DGLA was able to prevent UV-induced erythema presumably because the high dose was irritating to the skin. These results demonstrate that while DGLA and HETrE are not capable of treating or reversing UV induced erythema, these compositions unexpectedly were able to prevent UV-induced erythema.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

What is claimed is:

1. A method for preventing or reducing the occurrence of erythema on at least one area of the skin of a subject, the method comprising: topically applying a therapeutically effective amount of a composition comprising DGLA or 15-HETrE to the at least one area of skin of the subject.

2. The method of claim 1, wherein the composition comprises about 1.0 wt. % DGLA to about 20 wt. % DGLA.

3. The method of claim 2, wherein the composition comprises about 10 wt. % DGLA, about 1.0 wt. % DGLA, or about 0.1 wt. % DGLA.

4. The method of claim 1, wherein the composition comprises about 0.1 wt. % to about 50 wt. % 15-HETrE.

5. The method of claim 4, wherein the composition comprises about 10 wt. % 15-HETrE, about 1.0 wt. % 15-HETrE, about 0.1 wt. % 15-HETrE, or about 0.01 wt. % 15-HETrE.

6. The method of claim 1, wherein the erythema is caused by exposure to UV radiation.

7. The method of claim 1, wherein the composition is topically applied to at least one area of the skin prior to exposure of the subject to UV radiation.

8. The method of claim 1, wherein the composition is applied to the skin on a face, arms, torso, or legs.

9. The method of claim 1, wherein the composition further comprises a sunscreen active agent.

10. The method of claim 9, wherein the sunscreen active agent is a UV blocker, UV absorber, or UV scattering agent.

* * * * *